United States Patent
Hedmann et al.

(10) Patent No.: US 9,095,655 B2
(45) Date of Patent: Aug. 4, 2015

(54) APPARATUS FOR PERITONEAL DIALYSIS

(75) Inventors: Frank Hedmann, Volkach (DE); Stephan Klatte, Nienburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 319 days.

(21) Appl. No.: 12/493,846

(22) Filed: Jun. 29, 2009

(65) Prior Publication Data

US 2010/0004589 A1 Jan. 7, 2010

(30) Foreign Application Priority Data

Jul. 4, 2008 (DE) .......................... 10 2008 031 637
Jul. 31, 2008 (DE) .......................... 10 2008 035 742

(51) Int. Cl.
*A61M 1/28* (2006.01)

(52) U.S. Cl.
CPC ........... *A61M 1/285* (2013.01); *A61M 2205/70* (2013.01)

(58) Field of Classification Search
CPC ................ A61M 1/28–1/288; A61M 2205/70
USPC ............................... 604/27–31; 210/644, 645
See application file for complete search history.

(56) References Cited

U.S. PATENT DOCUMENTS

| | | | |
|---|---|---|---|
| 4,368,737 A | 1/1983 | Ash | |
| 4,618,343 A | 10/1986 | Polaschegg | |
| 4,898,576 A | 2/1990 | Philip | |
| 5,006,997 A | 4/1991 | Reich | |
| 5,141,493 A | 8/1992 | Jacobsen et al. | |
| 2005/0230313 A1* | 10/2005 | O'Mahony et al. | 210/645 |
| 2005/0234391 A1* | 10/2005 | Uesugi et al. | 604/24 |
| 2011/0160637 A1 | 6/2011 | Beiriger | |

FOREIGN PATENT DOCUMENTS

| | | |
|---|---|---|
| DE | 3333362 | 3/1986 |
| DE | 69215123 | 6/1997 |
| EP | 0498382 | 11/1996 |
| EP | 0644782 | 11/1998 |
| WO | WO 9527520 | 10/1995 |
| WO | WO 0130422 | 5/2001 |
| WO | WO 01/58509 | 8/2001 |

* cited by examiner

Primary Examiner — Kami A Bosworth
(74) Attorney, Agent, or Firm — Fish & Richardson P.C.

(57) ABSTRACT

This invention relates to a device for peritoneal dialysis with a means for the regular discharge and reuptake of dialysate, which comprises a conduit with a catheter, wherein a measurement bag is present, in which dialysate can be introduced, wherein first means are provided, with which the static pressure in the conduit between catheter and measurement bag can be determined, and second means are provided, by means of which the dialysate volume flow can be introduced into the measurement bag for a certain period. In accordance with the invention, third means are present, by means of which the volume of the dialysate introduced into the measurement bag can be determined, and furthermore fourth means are present, by which the catheter resistance substantially can be calculated from the values determined by the first to third means.

15 Claims, 1 Drawing Sheet

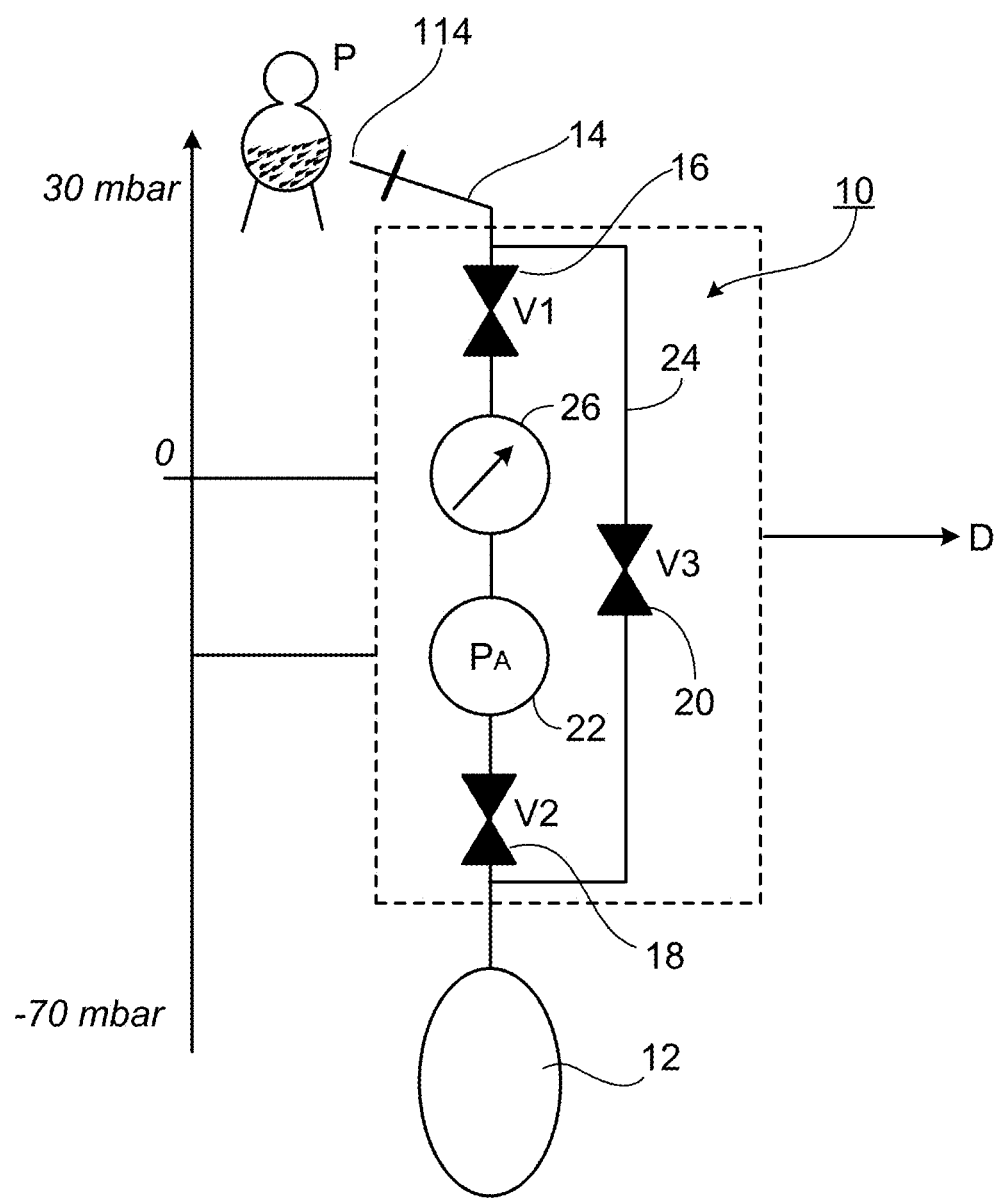

APPARATUS FOR PERITONEAL DIALYSIS

CROSS REFERENCE TO RELATED APPLICATION

This application claims priority under 35 U.S.C. §119(a) to German Patent Application No. 10 2008 031 637.7, filed Jul. 4, 2008, and German Patent Application No. 10 2008 035 742.1, filed Jul. 31, 2008, the entire contents of which are hereby incorporated by reference.

TECHNICAL FIELD

This invention relates to a device for peritoneal dialysis with a means for the regular discharge and reuptake of dialysate, which includes a conduit with a catheter.

BACKGROUND

Peritoneal dialysis is a variant of artificial hemodialysis, where the abdominal membrane (peritoneum) of the patient, which is well supplied with blood, is used as an endogenous filter membrane. Via a catheter, dialysate is introduced into the abdominal cavity. According to the principle of osmosis, urinary constituents are removed from the blood and enter the abdominal cavity. After a few hours, the dialysate with the urinary constituents is discharged from the abdominal cavity.

In principle, different possibilities exist for performing the peritoneal dialysis. In continuous ambulatory peritoneal dialysis (CAPD), the patients themselves replace the dialysate about four to five times a day. In automated peritoneal dialysis (APD), a device, the so-called cycler, performs the automatic bag replacement during the night, so that the patient still is independent during the day.

In automated peritoneal dialysis in which the abdominal cavity is filled by means of the aforementioned cycler, a volume control usually is performed to ensure that no more than a maximum filling volume is administered to the patient. In an average adult, this maximum filling volume for instance is 3500 ml. Usually, standardized values are used for the filling volume, as the effort for an experimental determination of the patient-specific filling volume should be avoided.

In peritoneal dialysis, an access to the abdominal cavity of the patient is provided. Typically, this access is provided by the so-called patient catheter, through which the exchange of fluid is effected. One end of this catheter opens into the abdominal cavity of the patient, and on the other side—outside the patient—a patient connector is provided, which offers a possibility for coupling to a tube system. In the course of time, the catheter can be clogged by deposits, so that its function can be restricted.

To ensure an unrestricted function, the catheter resistance presently is performed manually by the attending physician. A characteristic for the catheter resistance is calculated from the time required for the discharge of a certain volume flow of fluid.

SUMMARY

It is an object of the present invention to develop a device for peritoneal dialysis such that the device can automatically determine the catheter resistance.

Accordingly, there is provided a device for peritoneal dialysis with a means for the regular discharge and reuptake of dialysate (the so-called cycler), which includes a conduit with a catheter. In some embodiments of the invention, a measurement bag additionally is provided on the cycler, in which dialysate can be introduced. There are provided first means with which the static pressure in the conduit between catheter and measurement bag can be determined. In addition, second means are provided, by means of which the dialysate volume flow can be introduced into the measurement bag for a certain period. Third means are provided, with which the volume of the dialysate introduced into the measurement bag can be determined, and finally fourth means are provided, by which the catheter resistance substantially can be calculated from the values determined by the first to third means.

The first means can include a pressure sensor, by means of which the static pressure can be determined.

The second means advantageously include at least one time-controllable valve, in order to introduce the dialysate into the bag for a specified measurement period by means of an automatic valve control.

Furthermore, the third means preferably include a pump and a balancing unit, in order to determine the dialysate volume collected in the bag by discharging the dialysate from the measurement bag and passing it through the balancing unit.

Advantageously, a first valve, a pressure sensor, a pump and a second valve are arranged in series in the conduit between catheter and measurement bag.

Particularly advantageously, a bypass conduit in which a third valve is arranged is branched off from the conduit before the first valve. This bypass conduit opens into the conduit after the second valve.

With the device in accordance with the invention, the measurement of the catheter resistance can be performed automatically. It is conceivable to check the catheter resistance at the beginning of the treatment, so as to be able to react to possible deviations from a previously determined expected value. Storing the characteristic for the catheter resistance over several measurements also can provide information about a change in the catheter properties. For instance, this can be a measurement series of the values each determined before a treatment. Such measurement series can be stored on a patient card and before each treatment can be compared with the actually measured value.

With the device of some embodiments of the invention, the catheter resistance can be determined gravimetrically as follows:

$1^{st}$ step: levelling of the patient, i.e., determination of the static patient pressure;

$2^{nd}$ step: gravimetric drainage of the dialysate from the patient into a measurement bag, with the patient lying above the bag;

$3^{rd}$ step: levelling the bag by stopping the dialysate volume flow after a certain period and likewise statically levelling the bag;

$4^{th}$ step: volume balancing of the contents of the measurement bag when draining the measurement bag; and $5^{th}$ step: calculating the catheter flow resistance from the determined parameters volume and time.

DESCRIPTION OF DRAWINGS

Further details and advantages of the invention will be explained in detail with reference to an embodiment illustrated in the drawing.

FIG. 1 schematically shows a device in accordance with an embodiment the invention, with the components functionally necessary for the description of the device being represented as symbols.

DETAILED DESCRIPTION

Referring to FIG. 1, a patient P is charged with a sufficient volume of dialysate, which can be for instance 2000 ml of dialysate.

The patient P is connected with the so-called cycler 10, i.e., the device for the regular discharge and reuptake of dialysate. On the cycler 10, a measurement bag 12 of known volume is suspended. The measurement bag is disposed below (lower than) the patient. In the illustrated embodiment, the volume of the measurement bag at the beginning of the measurement is 0 ml. The measurement bag 12 is connected with the patient catheter 114 via a conduit 14. The flow resistance of the system of conduits is known. In the illustrated embodiment, this flow resistance—without the flow resistance of the patient catheter 114—can be $R_{system}=0.2$ mbar×min/ml.

During the measurement described below, the position of the patient P with respect to the measurement bag 12 should be rather constant.

At the beginning, the static pressure of the patient P is determined. For this purpose, the first valve 16 is opened, whereas the second valve 18 and the third valve 20 remain closed. In the illustrated embodiment, the static pressure is $P_{pat\,stat}=30$ mbar.

For determining the resistance, the dialysate is gravimetrically, i.e., by gravity, drained from the patient into the measurement bag 12 for a certain period x. This can be effected either via the first valve 16, the pump chamber of the pump 22 likewise arranged in the conduit, and the second valve 18, or via a bypass conduit 24 and the third valve 20 disposed in the bypass conduit 24. The period x is chosen such that a complete drainage of the patient is avoided. In the illustrated embodiment, a maximum volume flow of 300 ml/min is assumed. To achieve a good measurement result, a measurement time of x=3 min is chosen. This leads to an expected total volume in the measurement bag of about 900 ml, so that a complete drainage of the patient with dialysate can be avoided.

In the next step, the static pressure of the bag 12 is determined. For this purpose, the second valve 18 is opened, whereas the first valve 16 and the third valve 20 are closed. The static pressure of the bag 12, like the static pressure of the patient P, is measured by a pressure sensor 26, which is disposed in the conduit 14. In the illustrated embodiment, the measured static pressure is $P_{bag\,stat}=70$ mbar.

To determine the flown volume of dialysate, the measurement bag 12 is drained by means of the pump 22 into a drain D (not shown) via a flow path, and balanced and measured via a balancing unit (not shown). In the present embodiment, the actually measured volume from the measurement bag is $V_{bag}=600$ ml.

Via a calculation unit (not shown), the resistance of the patient catheter 114 is calculated from the measured and determined values as follows:

$1^{st}$ step: Calculation of the pressure difference between patient and bag:

$$P_{stat\,total}=P_{pat\,stat}+|P_{bag\,stat}|=30\text{ mbar}+|-70\text{ mbar}|=100\text{ mbar}$$

$2^{nd}$ step: Calculation of the flow rate:

$$Q=V_{bag}/T=600\text{ ml}/3\text{ min}=200\text{ ml/min}$$

$3^{rd}$ step: Calculation of the total conduit resistance of the system, including resistance of the patient catheter:

$$R=P_{stat\,total}/Q=100\text{ mbar}/200\text{ ml/min}=0.5\text{ mbar*min/ml}$$

$4^{th}$ step: Calculation of the patient catheter resistance:

$$R_{catheter}=R-R_{system}=0.5\text{ mbar*min/ml}-0.2\text{ mbar*min/ml}$$

$$R_{catheter}=0.3\text{ mbar*min/ml}$$

The invention claimed is:

1. A peritoneal dialysis device, comprising:
 a patient catheter configured to be disposed in and to be placed in fluid communication with a peritoneal cavity of a patient;
 a conduit configured to be fluidly connected to the patient catheter;
 a container that can be fluidly connected to the conduit such that dialysate can be transported from the peritoneal cavity of the patient to the container via the conduit and the patient catheter; and
 a pressure sensor positioned along the conduit between the patient catheter and the container,
 wherein the peritoneal dialysis device is programmed to calculate a resistance of the patient catheter as a function of a static pressure in the conduit between the patient catheter and the container and a flow rate of dialysate from the peritoneal cavity of the patient to the container.

2. The device of claim 1, wherein the peritoneal dialysis device is programmed to determine the static pressure in the conduit between the catheter and the container using the pressure sensor, and to determine the flow rate of dialysate delivered from the peritoneal cavity of the patient to the container.

3. The device of claim 2, further comprising a first valve positioned along the conduit between the patient catheter and the pressure sensor, and a second valve positioned along the conduit between the pressure sensor and the container, wherein the peritoneal dialysis device is programmed to open the first valve and close the second valve to measure the static pressure in the conduit between the catheter and the container.

4. The device of claim 1, further comprising at least one time-controlled valve positioned along the conduit between the patient catheter and the container, wherein the peritoneal dialysis device is programmed to open the at least one time-controlled valve for a period of time to allow the dialysate to flow from the peritoneal cavity of the patient to the container.

5. The device of claim 4, further comprising a pump that can be placed in fluid communication with the container to pump dialysate from the container, and a balancing unit that can be placed in fluid communication with the pump for determining a volume of dialysate pumped from the container.

6. The device of claim 5, wherein the peritoneal dialysis device is programmed to determine the flow rate of the dialysate as a function of the period of time during which the time-controlled valve is open and the volume of dialysate pumped from the container.

7. The device of claim 1, further comprising a first valve, a pump, and a second valve positioned along the conduit between the patient catheter and the container.

8. The device of claim 7, further comprising a bypass conduit in which a third valve is disposed, wherein the bypass conduit is connected to the conduit between the first valve and the patient catheter, and between the second valve and the container.

9. The device of claim 1, wherein the container is a bag.

10. The device of claim 1, wherein the peritoneal dialysis device comprises a calculating unit to calculate the resistance of the patient catheter as a function of the static pressure in the conduit between the patient catheter and the container and the flow rate of dialysate from the peritoneal cavity of the patient to the container.

11. The device of claim 1, wherein the peritoneal dialysis device is programmed to calculate the static pressure in the conduit between the patient catheter and the container as a sum of a static pressure of the patient and an absolute value of a static pressure of the container.

12. The device of claim 1, further comprising:
a first valve positioned along the conduit between the patient catheter and the pressure sensor; and
a second valve positioned along the conduit between the pressure sensor and the container,
wherein the peritoneal dialysis device is programmed to open the first valve and close the second valve to measure the static pressure in the conduit between the catheter and the container.

13. The device of claim 1, wherein the peritoneal dialysis device is programmed to calculate the resistance of the patient catheter as:

$$((P_{pat\,stat} + |P_{bag\,stat}|)/Q) - R_{system},$$

where $P_{pat\,stat}$ is a static pressure of the patient, $P_{bag\,stat}$ is a static pressure of the container, Q is the flow rate of the dialysate from the peritoneal cavity of the patient to the container, and $R_{system}$ is a known resistance of a system of conduits through which the dialysate flows during use.

14. A peritoneal dialysis device, comprising:
a patient catheter that can be placed in fluid communication with a peritoneal cavity of a patient;
a conduit that can be fluidly connected to the patient catheter;
a container that can be fluidly connected to the conduit such that dialysate can be transported from the peritoneal cavity of the patient to the container via the conduit and the patient catheter; and
a pressure sensor positioned along the conduit between the patient catheter and the container, wherein the peritoneal dialysis device is programmed to calculate a resistance of the patient catheter as a function of a static pressure in the conduit between the patient catheter and the container and a flow rate of dialysate from the peritoneal cavity of the patient to the container, and the peritoneal dialysis device is programmed to calculate the static pressure in the conduit between the patient catheter and the container as a sum of a static pressure of the patient and an absolute value of a static pressure of the container.

15. A peritoneal dialysis device, comprising:
a patient catheter that can be placed in fluid communication with a peritoneal cavity of a patient;
a conduit that can be fluidly connected to the patient catheter;
a container that can be fluidly connected to the conduit such that dialysate can be transported from the peritoneal cavity of the patient to the container via the conduit and the patient catheter; and
a pressure sensor positioned along the conduit between the patient catheter and the container,
wherein the peritoneal dialysis device is programmed to calculate a resistance of the patient catheter as:

$$((P_{pat\,stat} + |P_{bag\,stat}|)/Q) - R_{system},$$

where $P_{pat\,stat}$ is a static pressure of the patient, $P_{bag\,stat}$ is a static pressure of the container, Q is a flow rate of the dialysate from the peritoneal cavity of the patient to the container, and $R_{system}$ is a known resistance of a system of conduits through which the dialysate flows during use.

* * * * *